(12) United States Patent
Golesworthy

(10) Patent No.: US 8,246,673 B2
(45) Date of Patent: Aug. 21, 2012

(54) EXTERNAL SUPPORT FOR A BLOOD VESSEL

(75) Inventor: Taliesin John Golesworthy, Cheltenham (GB)

(73) Assignee: Exstent Limited, Tewkesbury, Gloucestershire (GB)

( * ) Notice: Subject to any disclaimer, the term of this patent is extended or adjusted under 35 U.S.C. 154(b) by 257 days.

(21) Appl. No.: 12/533,098

(22) Filed: Jul. 31, 2009

(65) Prior Publication Data

US 2009/0292349 A1    Nov. 26, 2009

Related U.S. Application Data

(63) Continuation-in-part of application No. 10/527,498, filed as application No. PCT/GB03/04135 on Sep. 18, 2003, now abandoned.

(30) Foreign Application Priority Data

Sep. 19, 2002   (GB) .................................. 0221781.8
Apr. 14, 2003   (GB) .................................. 0308517.2

(51) Int. Cl.
   *A61F 2/06* (2006.01)
(52) U.S. Cl. ..................................................... 623/1.13
(58) Field of Classification Search .................. 623/1.1,
   623/1.12, 1.13, 1.15, 1.19, 1.22, 1.3, 1.31,
   623/1.32, 1.34, 1.36, 1.42, 1.44, 11.11
   See application file for complete search history.

(56) References Cited

U.S. PATENT DOCUMENTS

| | | | |
|---|---|---|---|
| 3,626,947 A | 12/1971 | Sparks | |
| 4,904,254 A | 2/1990 | Lane | |
| 5,246,546 A | 9/1993 | Wilkinson | |
| 5,476,471 A | 12/1995 | Shifrin et al. | |
| 5,741,215 A | 4/1998 | D'Urso | |
| 6,112,109 A * | 8/2000 | D'Urso | 600/407 |
| 6,165,193 A | 12/2000 | Greene, Jr. et al. | |
| 6,197,050 B1 | 3/2001 | Eno et al. | |
| 6,436,132 B1 * | 8/2002 | Patel et al. | 623/1.13 |
| 6,554,856 B1 | 4/2003 | Doorly et al. | |
| 6,648,911 B1 * | 11/2003 | Sirhan et al. | 623/1.15 |
| 6,899,728 B1 | 5/2005 | Phillips et al. | |
| 7,073,456 B2 | 7/2006 | Phillips et al. | |
| 7,290,494 B2 | 11/2007 | Phillips et al. | |
| 2002/0068968 A1 | 6/2002 | Hupp | |
| 2002/0103527 A1 | 8/2002 | Kocur et al. | |
| 2006/0036311 A1 | 2/2006 | Nakayama et al. | |
| 2006/0129228 A1 | 6/2006 | Golesworthy et al. | |

FOREIGN PATENT DOCUMENTS

| | | |
|---|---|---|
| EP | 1055401 A1 | 11/2000 |
| GB | 2090143 A | 7/1982 |
| GB | 2344053 A | 5/2000 |
| WO | 9740755 A1 | 11/1997 |
| WO | 0239906 A2 | 5/2002 |

* cited by examiner

*Primary Examiner* — Tuan V Nguyen
(74) *Attorney, Agent, or Firm* — Porzio, Bromberg & Newman, P.C.

(57) ABSTRACT

There is provided a support adapted for location exteriorly of a blood vessel, the support being locatable around the blood vessel and shaped to be in morphological relationship with the blood vessel, in which the support is formed from a settable material and the support is capable of being formed into a tube; and a method of morphometric analysis of a patient's blood vessel using an imaging scanner which method has the steps of:
   (i) obtaining a diametral cross-sectional image of the blood vessel;
   (ii) obtaining a pseudo-transverse cross-section image of the blood vessel; and
   (iii) processing the images from steps (i) and (ii) to construct a morphometric model of the blood vessel.

9 Claims, 8 Drawing Sheets

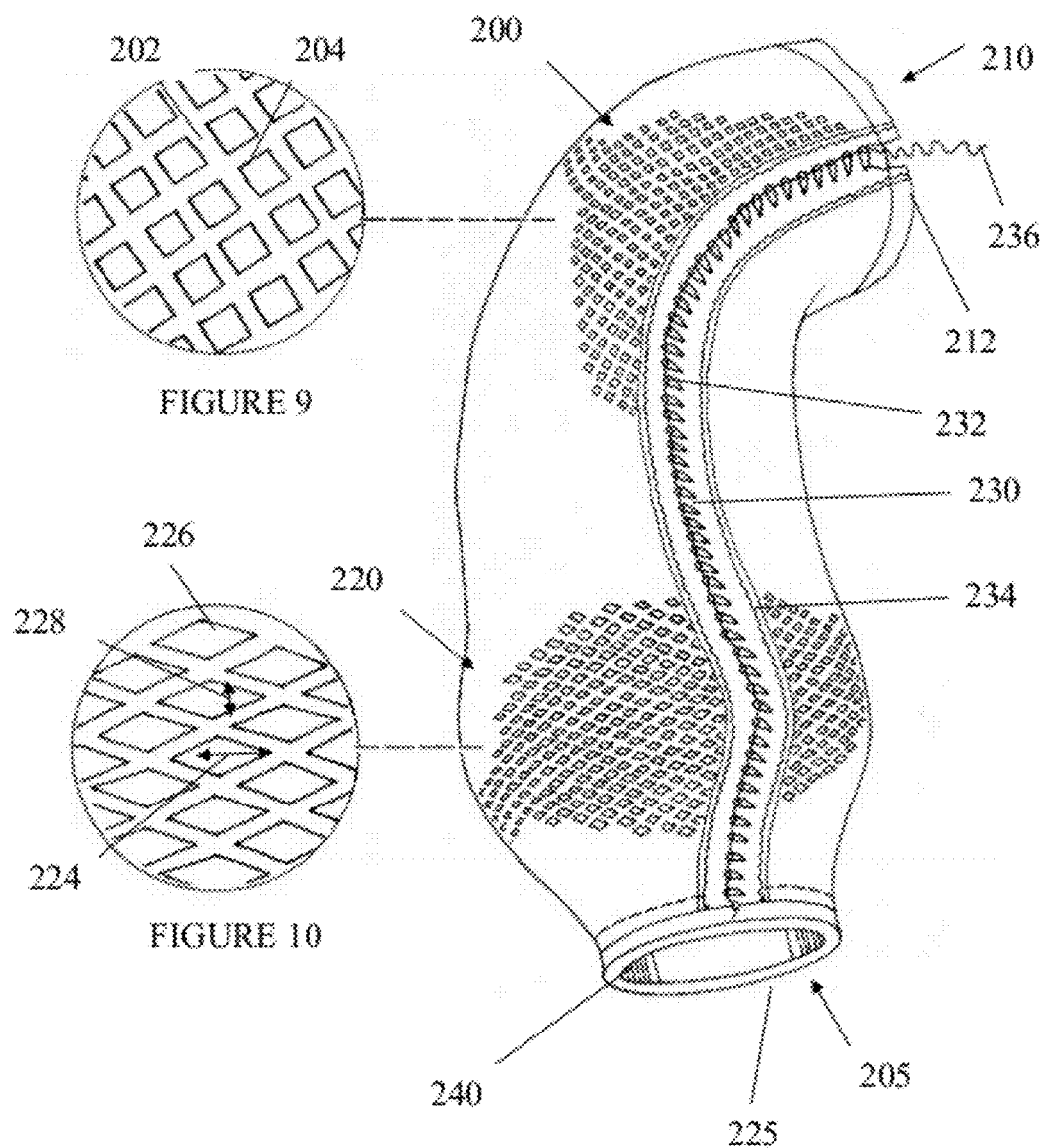

EXTERNAL SUPPORT FOR A BLOOD VESSEL

CROSS REFERENCE TO RELATED APPLICATION

This application is a continuation-in-part of U.S. patent application Ser. No. 10/527,498 filed Oct. 11, 2005, which is abandoned, which is a National Stage entry of PCT/GB2003/004135 filed 18 Sep. 2003, the entirety of each of which is hereby incorporated by reference into this application.

BACKGROUND OF THE INVENTION

Field of the Invention

This invention concerns improvements in or relating to stents for use in humans.

The present invention has particular but not exclusive reference to a stent for use in association with the ascending aorta.

Aortic dissection is or can be a fatal occurrence since the rupture of the artery occasions dramatic haemorrhaging resulting in system failure. One particular condition afflicting a significant number of people is that known as Marfan's Syndrome which affects the connective tissue in the body to the extent that the aortic root becomes a focus for weakening in time with the pulsing of the blood flow from the heart. The tissue of which the artery is made is weakened and accordingly stretches with a concomitant increase in the diameter of the artery giving rise to dissection or aneurysm. The wall of the artery becomes thinner in section and should distension increase further rupture will occur with the results indicated supra. In addition, the aortic valve is formed at the base of the aorta and the distension thereof additionally and adversely affects the operational efficiency of the valve with leakage occurring.

Of course, aortic root dissection is not confined to sufferers of Marfan's Syndrome and can affect any one.

Conventionally the surgical procedures for addressing the problem, either electively or on an emergency basis, involve the insertion of a stent in the aorta or the removal of the aortic root and its replacement with a prosthetic replacement aorta incorporating a mechanical valve, or in some cases a pig's valve, the prosthesis being sutured in place. In an alternative procedure the patient's own aortic valve leaflets are inserted within the prosthetic aorta. These procedures do, however, involve considerable expenditure in both time and cost. The deployment of a heart/lung bypass machine is required with all the dangers of infection associated with such intrusive procedures. Post-operatively because of the intimate contact between the blood and the now installed internal replacement root and valve combination a continuing risk of infection remains without limit as to time. Patients having undergone such surgery have to be continuously mindful of the need to secure antibiotic protection whenever potentially intrusive activity on the body is contemplate, for example dentistry. Furthermore due to the increased risk of clotting following surgery of this kind anti-coagulants have to be administered usually on a daily basis with blood tests to check the INR being necessary regularly, thus adding to the on-going cost of patient care.

The conventional stents deployed internally are generally produced from synthetic material one example of which is that available under the trade name DACRON®, a polyester with tough elastic properties. In some designs of internal stent reinforcement giving a degree of rigidity coupled with flexibility is provided and may take the form of a spirally wound open-coiled or mesh insert. The flexibility is necessary to accommodate differing tortuosity of arteries, but the rigidity is also required to resist deformation by kinking for example.

Conventional internal stents for treating aneurysms are available in a range of sizes to fit as appropriate. However the stents do not mould to the internal contours of the distended artery at the point of the aneurysm. The internal stents locate within the artery either side of the aneurysm and accordingly pockets may be formed externally of the stent but within the artery and these pockets may contain blood. In the case of aortic root replacement by removal of the root and substitution with a prosthesis and valve, the diameter of the prosthesis is chosen to match either the exit aperture in the left ventricle, if the valve is to be replaced, or to the lower section of the artery if the valve is not to be replaced. Accordingly the graft of the prosthesis onto the upper end of the aorta adjacent the aortic arch tends not to be such a good fit.

An object of the present invention is to provide a new and improved stent that supports the external surface of the patient's own aorta and obviates the need for procedures of such an intrusive character as are currently required.

A further object of the invention is to provide a method of manufacturing the new and improved stent whereby the resultant stent is of customised form.

According to a first aspect of the present invention there is provided a stent adapted for location exteriorly of a blood vessel, the stent being formed in such manner as to be locatable around and in morphological relationship with the said blood vessel, and means for maintaining the stent in such relationship with the blood vessel.

The stent may include a sleeve that may be in one or two parts and of generally cylindrical form but may include one or more sections of varying form in order to conform to the morphological requirements in any particular case.

The sleeve is provided with appropriately located recesses or apertures for accommodating other interconnecting blood vessels or structures contiguous with the blood vessel being supported by the stent.

The sleeve of the stent may be provided with a base or flange portion for attachment to a main heart structure, for example the ventricle muscle, such that a securement or anchor point is established for the stent. The base or flange portion may be adapted for appropriate suturing or other means to the said structure. For example the other means may include stapling or adhesion.

In an alternative form of the stent of the present invention the sleeve may not be required to be secured to the heart structure and may be of such morphological size-matching to the blood vessel as to obviate the need for additional securement. In such event the stent effectively moulds to the shape of the blood vessel, e.g. the ascending aorta, and in this manner provides the necessary support and positive location as required. In one embodiment the stent may be tapered at either end in opposite directions such that when in position on the vessel, the stent locks in position and is thus maintained in its appropriate location.

The interconnection of the parts of the sleeve may be effected by a hinge mechanism with releasable latches provided at the mating edges of the parts.

In the alternative, the sleeve may be of resilient material slit longitudinally to allow it to be expanded over the wall of the artery and then to recover its original condition, the sleeve being suitably clampable in position embracing the artery in the said morphological relationship. The clamping may be achieved by the application of suitable ties, for example those known as cable ties which lock firmly around the sleeve, which may be provided with one or more grooves for receiving and locating the ties. The clamping may alternatively be effected by the insertion of a locking pin extendable through hinge elements provided at the mating edges of the slit in the sleeve.

It will be appreciated that other means of securing together the parts of the stent sleeve may be adopted without departing from the present invention. For example zip fasteners appropriately designed to avoid the presence of surfaces that may snag and provided with suitable means for this purpose. In particular the surface of the fastener in contact with the blood vessel, e.g. the aorta, should be of such character as not to give rise to fretting. In this respect a protective flap could be provided.

The sleeve of the stent may be of varying thickness with the greatest thickness being provided in the base or flange region thereof to provide strength at the point of attachment. The thickness may therefore reduce away from that region to afford a degree of flexing given the need to accommodate the pulsing of the blood through the artery.

The sleeve may have an outer casing and a relatively inner casing, the outer casing being of more rigid construction than the inner casing which latter may be configured to provide the flexure mentioned above. In this connection the inner casing may be of petal-like form to encompass the artery but to allow flexing.

In an alternative embodiment the stent of the present invention is formed of one or more parts of spiral formation whereby when in position around the blood vessel close support is given thereto. An advantage of this embodiment lies in its potential for feeding on to the vessel and reforming into a spirally wound coil to provide a unitary support. In position the spiral formation may form either an open coil or a closed coil and may accordingly constitute a former like structure surrounding the blood vessel. This embodiment may be in one or more sections dependent upon the axial length and form required. Suitable interconnections for the sections are provided and may be in the form of screw fitments or their equivalent whereby upon tightening the coil embraces and supports the blood vessel.

The spiral form of stent of the present invention may allow tissue growth within its interstices thereby serving to enhance its integrity in relation to the blood vessel and concomitantly its strength.

The inner surface of the stent must be of a smoothness to ensure that no fretting or abrasion occurs and for similar reasons the external surface of the stent must equally be tolerant of other adjacent body parts, for example other blood vessels or the pericardial wall.

The inner surface of the stent may be suitably contoured or profiled to minimise fretting or abrasion and to assist in the egress of metabolites that may issue from the outer surface of the blood vessel into contact with the stent. The inner surface of the stent may in this even assist in the movement of the metabolites into the pericardial space possibly with a peristaltic effect. Further, the contouring or customising of the stent in this fashion assists in restricting axial movement of the blood vessel, e.g. the aorta, tending thereby to ensure the containment of the vessel within the limits of the stent. The stent thus acts as a mechanical barrier to axial as well as diametral movement of the blood vessel.

The material from which the stent is produced must possess structural integrity in terms of its burst strength, bend strength, tensile strength, liquid porosity, load distribution and general security particularly for mounting to the heart muscle. Further the material should possess a degree of opacity but should be translucent for the purposes of allowing non-intrusive investigative procedures to take place, for example MRI scanning. The material should, however, be resistant to the effect of electro-magnetic fields.

The material must also be thermally stable given the potentially variable nature of its working environment and has to be biocompatible in terms of its location within the body structure. In particular, it must possess mechanical, chemical, thermal, proteinal, enzymal and pericardial fluid biocompatibility and resistance to attack from any of these sources.

The material from which the stent may be made may contain antibiotics gradually releasable in time, the antibiotic elements being incorporated during the manufacture of the stent.

The material from which the stent may be made may be polymeric, metallic, or ceramic or appropriate mixtures thereof to meet the requirements of strength and compatibility hereinbefore mentioned. Another material that may be appropriate is a heat shrink plastics material that would be recoverable in terms of shape either immediately or over a period of time to produce the morphological fit, which is an important novel and inventive step of the present invention. The recovery of the plastics material may be in-built such that it occurs over a period of time or in the alternative the recovery could be triggered by appropriate external means.

The material from which the stent may be produced may be polymeric polypropylene, polyester, PTFE or a polyoxymethylene homopolymer such as that available from Du Pont under the name DELRIN®, or a ultra high molecular weight polyethylene. Further, the polymeric material may have applied thereto embroidery of suitable material, for example suture material.

In general the stent of the invention may be of such form as to be adjustable following its initial application to the affected blood vessel. Such adjustment may be capable of initiation externally of the patient's body and may be electronic.

According to a second aspect of the invention there is provided a method of manufacturing a stent according to the first aspect for morphologically fitting an artery including the steps of producing a computerised 3D model from a scanned image of the artery to which the stent is in practice to be applied, and rapid prototyping the computerised 3D model in an appropriate material to provide the stent or a mould for the stent or a precursor therefor.

As indicated supra the material from which the stent may be made may be polymeric and there may be applied thereto a woven or embroidered structure made of for example suture thread. One method of making the morphological form of stent according to the second aspect of the invention is to generate a thin polymeric shell of appropriate form and then to lay down thereon a meshwork of filamentary material to produce a embroidered or textile layer of its own inherent integrity on the surface of the polymeric shell which acts as a former for the stent. Once the embroidery has been completed the polymeric material is removed by suitable means, for example by thermal, chemical or solvent means thus leaving the morphologically shaped stent constituted by the woven structure. In order for the stent to be capable of application to a blood vessel, it would be necessary to incise the stent to allow entry thereinto of the vessel and then to resuture the free edges to provide a complete supporting structure surrounding the vessel.

In a further method of producing the stent of the present invention, again a thin 3-dimensional shell is produced from polymeric material conforming to the morphological profile of the vessel for which the stent is intended. The stent is generated by heat forming, machining, rapid prototyping or similar process and is then mounted in a computer numerically controlled machine having multi-axis control. Appropriate perforations in the shell are then machined in to provide the requisite apertures and other features with the apposite mechanical properties. The machining may be accomplished using one or more of a variety of processes, viz. water jet cutting, laser cutting, drilling or other appropriate machining methods.

A still further method involves the use of a flaccid support which mimics the three-dimensional morphology of the desired form and the application thereto of an embroidered or woven structure using a computer numerically controlled machine incorporating variable support radius. Once the embroidered woven layer is laid down on the flaccid support, the combination may then be used as the finished stent with suitable entry formations for application to the blood vessel. The flaccid support is dissolved away leaving the woven structure for application in the manner indicated.

A further method of producing the stent includes the steps of opening the thorax of the patient, the applying a polymeric wrap by hand to an approximate fit around the blood vessel and thermally treating the wrap to fix it in situ to the shape of the vessel, and closing the thorax.

A still further method of producing the stent includes the steps of opening the thorax and the pericardium, applying shuttering to the blood vessel, injecting room temperature vulcanising (RTV) or room temperature curing polymer around the blood vessel and within the shuttering, allowing the setting of the polymer, removing the shuttering and closing the thorax.

A third aspect of the invention is a stent made in accordance with the following method.

The scanned image may be generated for example from an MRI procedure applied to the affected artery of the patient and is then computerised and converted into a stent design. Other investigative procedures may be adopted for the initial imaging step, for example MRA, X-ray CT, 3D pulsed Doppler Echo measuring, namely a 3D version of 2D echocardiography used for aortic root measurement, and any other appropriate imaging technique. Suitable CAD software is employed to create the requisite customised 3D model of the affected artery and this image is then utilised for the rapid prototyping stage. The rapid prototyping, conventionally known in its abbreviated form as 'RP', is conducted on a suitable machine in which is produced in a suitable material a three-dimensional reproduction of the CAD image. The RP reproduction may give the actual stent or may provide the model from which the stent may be produced. In this latter respect, the model may be used to generate a mould from which the stent may be produced, in a similar vein to the 'lost wax' process. In either case the stent so generated is customised for the individual patient and contrasts sharply with the current procedures using internally applied stents of stock sizes.

The RP method may employ Stereo Lithography (SLA), Selective Laser Sintering (SLS) Solid ground curing (SOLIDER) Laminated object manufacturing (LOM) Fused deposition modelling (FDM) or Computer Numerical Controlled (CNC) machining for producing the stent.

The present invention will now be described by way of example only with respect to the accompanying drawings wherein:

FIG. 8 shows a schematic perspective view of a support according to the invention;

FIG. 9 shows a schematic expanded view of mesh used to form the support shown in FIG. 8; and FIG. 10 shows a schematic expanded view of mesh used in a first more supportive region of the support shown in FIG. 8.

Figure 1:
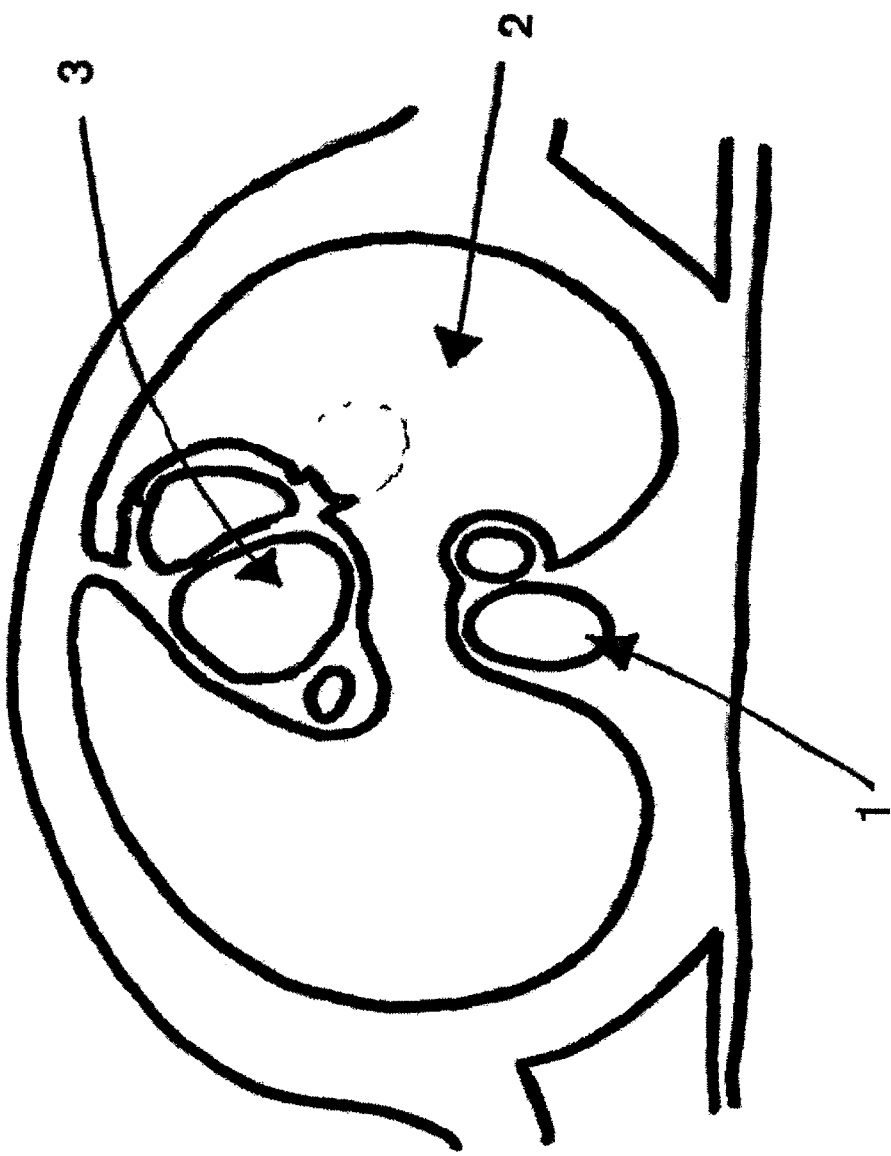
FIG. 1 shows a typical horizontal section through a human thorax clearly indicating the structures of the heart.

In the practice of the present invention the patient is first scanned using a standard medical MRI unit. For example, the scans are taken of the affected structure, e.g. ascending aorta, in such a way as to provide adjacent images substantially axial to the plane of the aorta. Poor quality images may be enhanced by multiple imaging and averaging/superposition of identical images. In some cases it may be appropriate to sedate the patient to improve image quality. FIG. 1 below shows a typical horizontal section through a human thorax clearly indicating the structures of the heart. Reference numeral 1 indicates the spine at the rear of the thorax, 2 indicates the left lung and 3 the structures of the heart.

Figure 2:
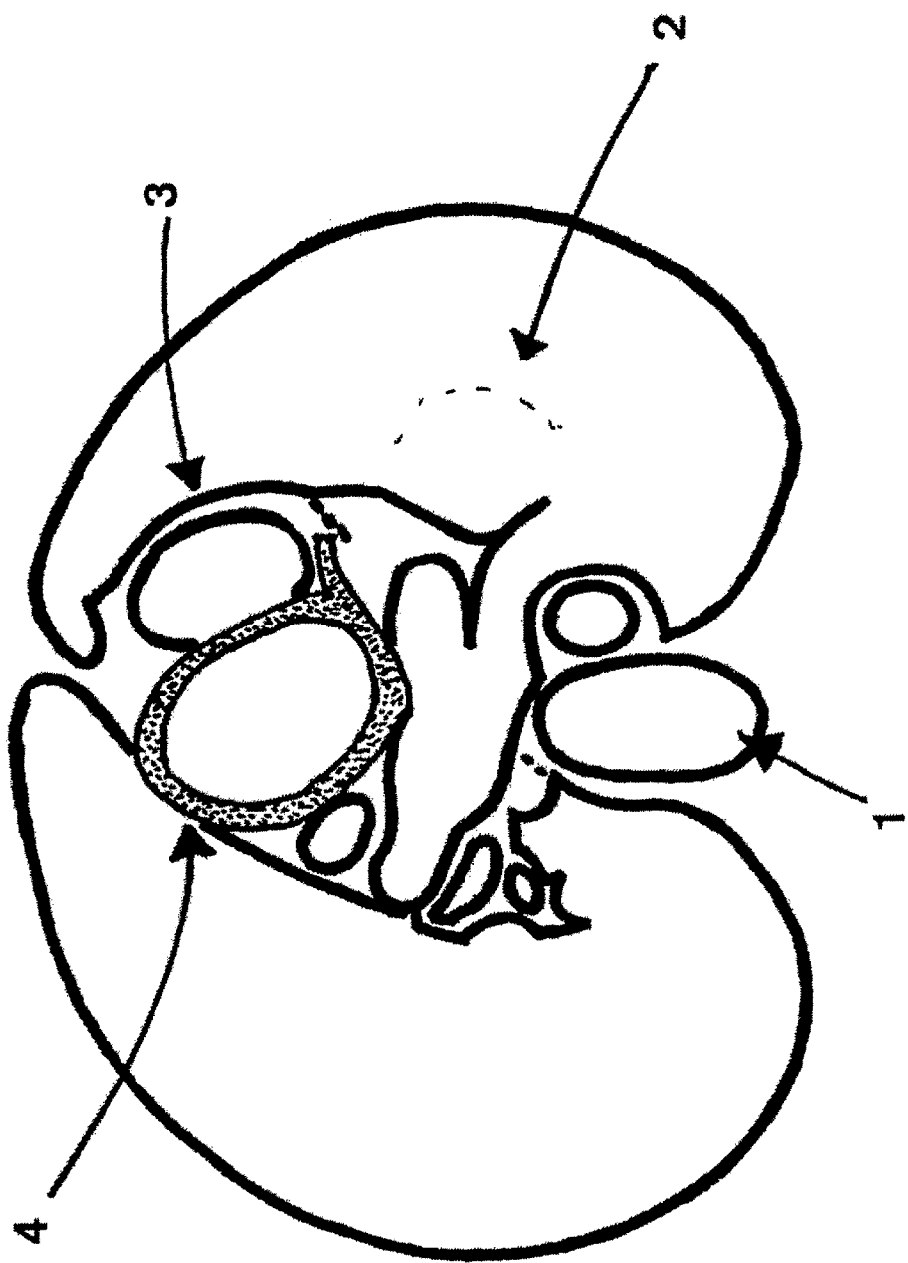
FIG. 2 shows a digitally highlighted horizontal section of the ascending aorta taken from a thoracic MRI image.

After the images have been taken, they are transferred to a standard PC computer running appropriate 3-dimensional computer aided design (CAD) software. A number of proprietary CAD packages are available a number of which are suited for the reconstruction of anatomical structures such as the ascending aorta. The MRI thoracic slice images are processed using image analysis software to extract the desired structure, in this case the ascending aorta (from the aortic annulus to the aortic arch). FIG. 2 shows a similar MRI horizontal section through a human thorax including the spine 1, the left lung 2, the heart 3 and a section of the ascending aorta digitally highlighted at 4.

Figure 3:
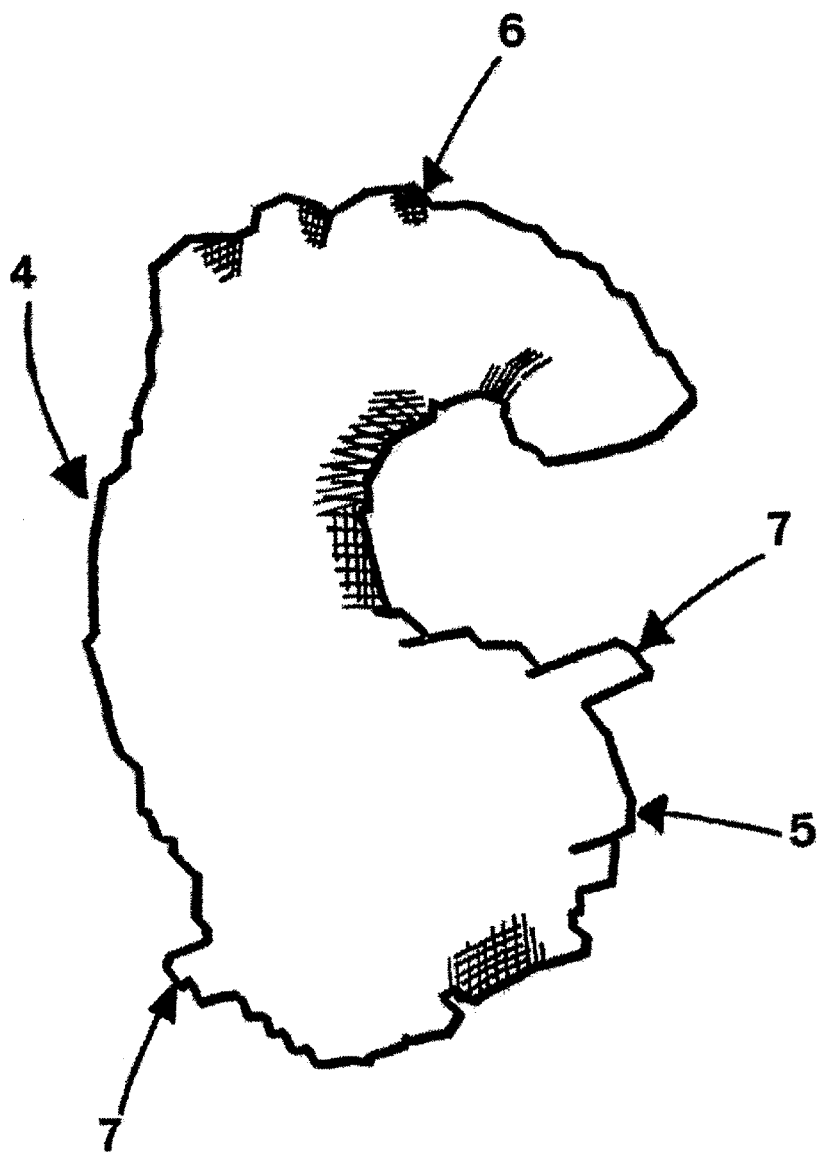
FIG. 3 shows a CAD reconstruction of an ascending aorta and aortic arch.

The aortic slices are then reconstructed within the CAD software using the image data and positional data from the MRI data files. FIG. 3 shows a CAD reconstruction including the ascending aorta 4, the aortic root containing the aortic valve 5, the aortic arch 6 and the coronary artery origins 7.

Figure 4:
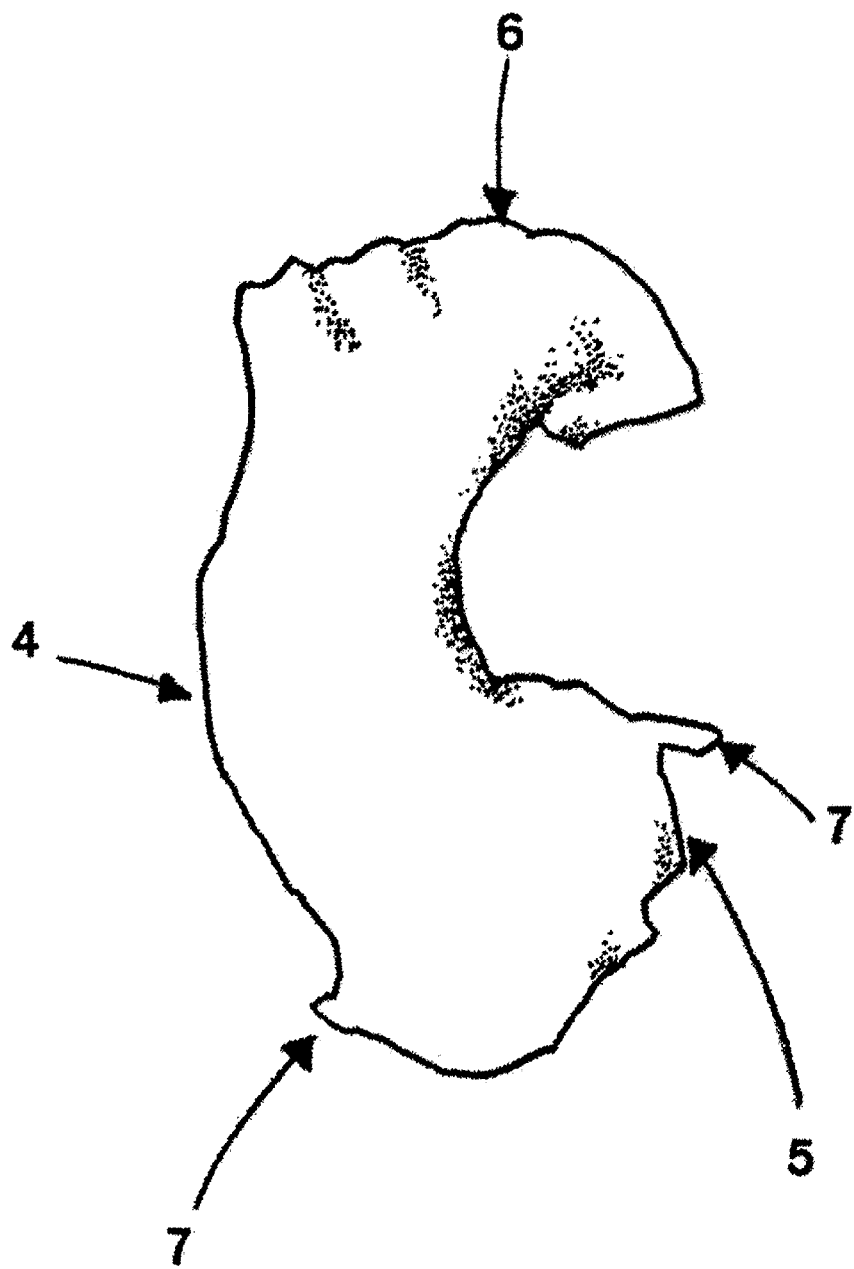
FIG. 4 shows a CAD reconstruction of an ascending aorta and aortic arch post smoothing.

Appropriate smoothing algorithms within the CAD software are used to interpolate between successive MRI images to produce a naturally contoured CAD model. Care must be taken, in the case of the ascending aorta, in correctly identifying and positioning the coronary arteries. This process is best done by examination of the MRI images by an appropriately qualified anatomist/surgeon. FIG. 4 shows a CAD model of the same ascending aorta 4, aortic root 5, aortic arch 6 and coronary origins 7, post smoothing.

Figure 5:
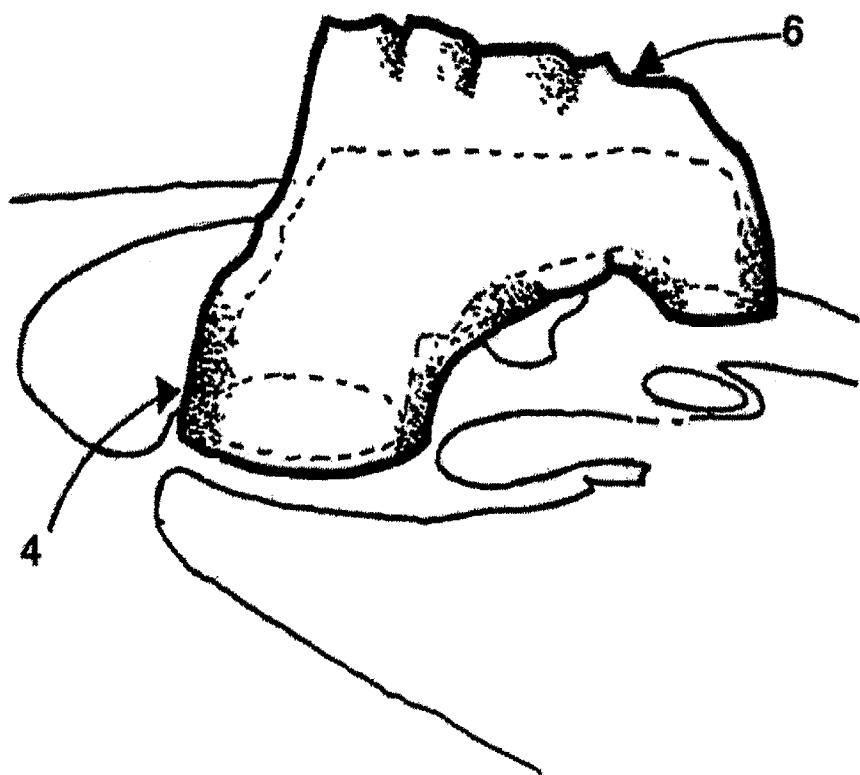
FIG. 5 shows a superimposition of a CAD reconstruction of an ascending aorta with one of the source MRI data files superimposed in the correct spatial position.

The CAD model can be validated within some CAD packages by superimposition of base MRI image data onto the finished CAD model. FIG. 5 below shows the superimposition of the CAD reconstruction with an MRI image slice from the source data. Structures visible include the upper part of the ascending aorta 4 and the aortic arch 6.

The CAD model can then be used to manufacture a tool from which the stent can be manufactured. Depending on the manufacturing method, the physical model can be manufactured as follows: The CAD model file can be transferred to an appropriate Rapid Prototyping machine, eg a stereo lithography machine (SLA) to produce a physical model of the ascending aorta in a polymer, e.g. UV curable epoxy resin. This model can then be used to produce a mould in a silicone rubber. The mould can then be used to produce daughter models of the aorta. Other manufacturing techniques can be used, for example selective laser sintering (SLS), CNC machining etc.

Figure 6:
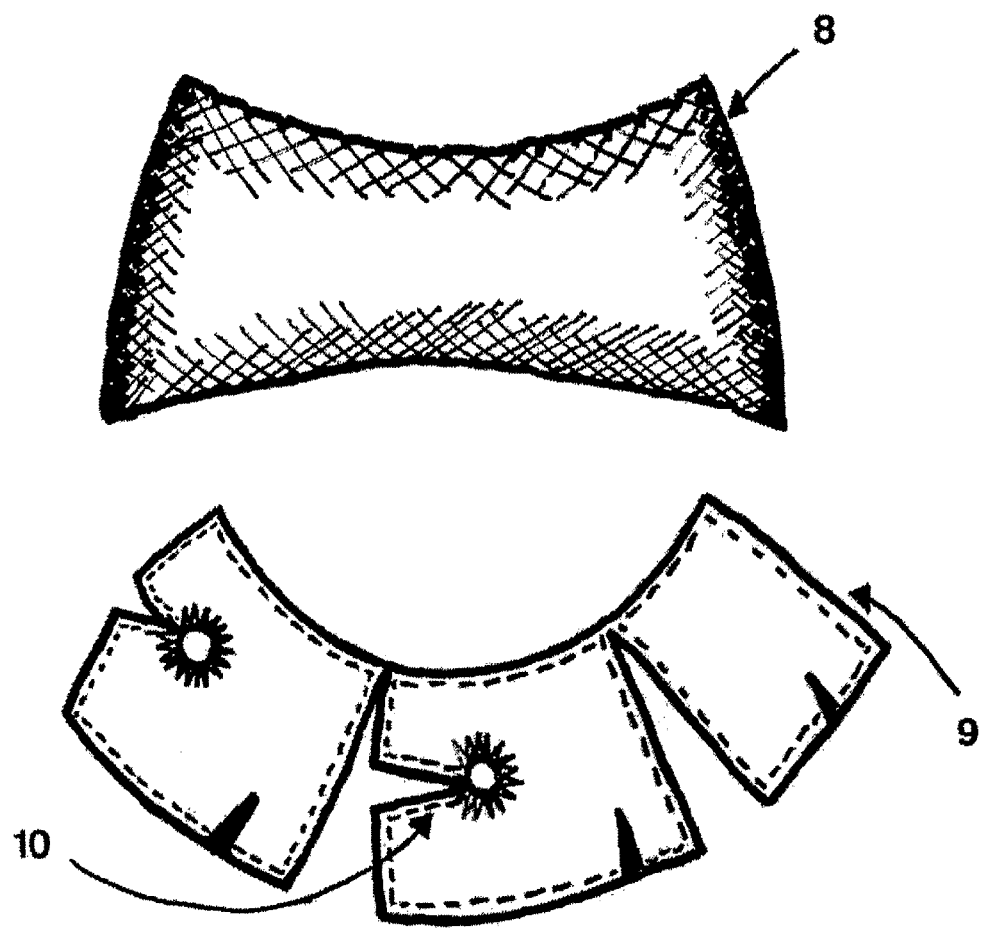
FIG. 6 shows an external support in 2 pieces.

The physical models thus produced are then used in a number of manufacturing processes to produce the finished stent:

Embroidering: Linear dimensional data are taken from a 2 dimensional projection of the 3 dimensional CAD reconstruction and used to produce a number of components on a standard computer controlled embroidering machine. The components are embroidered in a medical grade, multi-filament suturing thread, e.g. Polyester to produce an open structured net. The components are embroidered onto a water-soluble polymeric sheet in the CNC embroidering machine. Post-production, the water-soluble sheet is dissolved away and the components are stitched together, assuming their 3 dimensional shape during collocation. The finished stent is then sterilised, for example by steam heating, irradiation etc, prior to packing and transit to the surgeon for implantation. FIG. 6 shows an external stent manufactured in 2 components which, when sutured together assume the 3 dimensional shape. The 2 pieces fit the ascending aorta 8 and the aortic root 9 and include manufactured access within the aortic root section for the coronary origins 10.

Heat setting: A medical grade open structure mesh tube of multifilament, heat shrinkable, polymer is obtained of a diameter suitable to fit the largest outside diameter of the structure to be supported. The 3-dimensional CAD reconstruction of the structure is transferred to a Rapid Prototyping machine, eg Stereo Lithography (SLA) or Selective Laser Sintering (SLS) and a 3-dimensional physical model is produced in an appropriate polymer, e.g. an epoxide. This model is then used to produce a mould, for example a split mould, in an appropriate material, e.g. silicone rubber. From the mould, a solid pattern is produced. A suitably sized section of the heat shrinkable polymer mesh tube is slipped over the pattern and the two components are placed in a laboratory oven for an appropriate time at an appropriate temperature (to suit the characteristics of the polymer in question). After this exposure, the pattern and polymer mesh are removed from the oven. The polymeric mesh tube has shrunk to conform to the morphology of the pattern to a very high degree of accuracy to form the external stent. The stent is then removed from the pattern, for example by cutting an axial line along the stent in the anterior position with regard to the patient's thorax. The stent is then appropriately sterilised, packaged, and sent to the surgeon for implantation.

Vacuum deposition: The 3-dimensional CAD reconstruction of the bodily structure is transferred to a Rapid Prototyping machine from which a 3 dimensional physical model is produced. This model is either gas porous of itself or is used to model a rigid mesh, e.g. metallic mesh, that is gas porous. The gas porous pattern is then mounted in a vacuum deposition manufacturing machine wherein air is drawn through the gas porous pattern within an enclosed chamber. A "cloud" of appropriate polymeric fibres is introduced into the chamber and drawn onto the outside of the gas porous pattern by the airflow through the pattern. When a deposited "felt" of fibres has formed of appropriate thickness, controllable by time and fibre feed rate, and density, controllable by air flow rate through the gas porous pattern, the pattern and its attendant "felt" is transferred to an oven where the fibres are thermally bonded to each other by exposure in said oven for an appropriate time at an appropriate temperature, both being dependent on the selected polymer fibre. When the consolidated felt stent is removed from the oven it is separated from the gas porous pattern, e.g. by collapsing the pattern or cutting the stent, sterilised, packed and sent to the surgeon.

In all cases, surgical implantation is effected by conventional means using existing surgical procedures to reveal the ascending aorta from the aortic annulus to the arch and accommodating the coronary arteries. Said means would include for example surgical sub-procedures taken from the Ross procedure to expose the aortic annulus.

The stent of the invention conforms morphologically to the contours of the affected artery and when applied effectively provides a clamped sleeve to support its exterior in substantially full contact therewith. In the case of an aortic root the clamping of the sleeve also provides an adjustment for the aortic valve in terms of repositioning the valve seat to reinstate or reinforce integrity to prevent leakage at this location, thus avoiding the need to replace the valve.

The present invention does not require the high degree of invasive surgery associated with conventional surgical procedures for aortic root resection and valve replacement. Importantly also when the stent is in place although clearly it is in contact with bodily fluids and internal features of the pericardium and neighbouring parts, its external nature means that it is not in contact with blood. This very facet of the invention is of high benefit in terms of avoiding the possibility of infection affecting the blood stream and also obviates or significantly reduces the dependency of the patient, having undergone the successful procedure, on aftercare and drugs and treatment associated therewith. Quite apart from these advantages the avoidance of such invasive surgery is clearly less traumatic for the patient.

Beating heart surgery thus becomes a possibility by virtue of the present invention, which provides a bespoke stent. Indeed with some forms of the stent, for example the spirally wound version, the opportunity arises for keyhole surgery with all the attendant advantages which that offers in terms of non-intrusive procedures with less patient trauma and post-operative care and medication.

It will be appreciated that whilst the present invention has been described principally with reference to aortic root resection, it has a wider applicability generally to the treatment of aneurysms in any blood vessel and accordingly any reference herein to 'arteries' is to be construed in the wider context of blood vessels generally.

In a further aspect, this invention relates to a support for a blood vessel for use in reducing the risk of rupture of the blood vessel. The support of the invention is particularly suitable for use with the ascending aorta.

Rupture or dissection of the ascending aorta can be a fatal occurrence because it can result in dramatic haemorrhaging from this blood vessel and consequent system failure. Although it can affect anyone, sufferers of conditions known as Marfan's Syndrome and Bicuspid Aortic Valve Disease (BAVD) have an increased risk of rupture of the ascending aorta.

Marfan's Syndrome affects the connective tissue in the body to the extent that the aortic root becomes a focus for weakening in time with the pulsing of the blood flow from the heart. The arterial tissue stretches, resulting in an increase in the diameter of the artery which leads to dissection or aneurysm. In addition, the distension of the artery can adversely affect the efficiency of the aortic valve and leakage may occur.

Sufferers of BAVD have an aortic valve with only two leaflets or cusps instead of the normal three. BAVD is the most common form of congenital heart disease. It is associated with enlargement of the aorta and aortic aneurysm. The enlargement of the aorta tends to occur further away from the aortic annulus (i.e. where the aorta meets the heart) than in Marfan's Syndrome.

The problems with existing supports or stents for use with a patient with Marfan's syndrome are as set out above in paragraphs [003] to [007] of applicant's earlier patent publication no. WO 2004/026178. This patent publication describes a two piece stent or support that is adapted for location exteriorly of a blood vessel in morphological relationship with it. Such a support is time consuming for a surgeon to use.

One way in which the supports of WO 2004/026178 have been manufactured such that they are shaped to be in morphological relationship with a patient's blood vessel is to manufacture the support in accordance with a computer-aided design (CAD) model of the blood vessel. For example, when modelling a patient's aorta it has been necessary to collect a set of adjacent 2-dimensional image slices of the aorta using an MRI scanner and then reconstruct a 3-dimensional CAD model by stacking the 2-dimensional slices one on top of the other. A disadvantage of this method is that it is difficult to obtain suitable successive 2-dimensional images due to patient movement, e.g. breathing, within the scanner. Also, patient fatigue can be a problem due to the time that it takes to collect an appropriate number of images. In addition, MRI scanners are enclosed spaces and can induce claustrophobia in the patient.

An alternative device for application to a blood vessel is shown in U.S. Pat. No. 5,476,471 in the name of Shifrin et al. The device described in this document is not in morphological relationship with the blood vessel, but instead it has a rigid structure that imposes its own morphology on the blood vessel in order to compress a venous junction. The device is formed from metal in order to provide the rigid structure.

Improvements to external supports and their manufacture are continuously sought in order to reduce any difficulties experienced by the patient and to make it easier for a surgeon to apply the external supports to a blood vessel.

According to the invention there is provided a first support adapted for location exteriorly of a blood vessel, the support being locatable around the blood vessel and shaped to be in morphological relationship with the blood vessel, wherein the support is a single piece dense mesh which may be formed into a tube. This results in a support that is easier to manufacture and easier to implant than prior art supports.

According to the invention there is also provided a second support adapted for location exteriorly of a blood vessel, the support being locatable around the blood vessel and shaped to be in morphological relationship with the blood vessel, wherein the support is formed from a settable material and wherein the support may be formed into a tube. This provides a support that can more easily be provided in morphological relationship with the blood vessel. A reference to a support according to the invention herein should be understood to be a reference to a first and/or a second support according to the invention.

By referring to the support as being in (or having a) morphological relationship with the blood vessel, it is optionally meant that the support is pre-formed with a shape that morphometrically corresponds to the shape of the patient's blood vessel, e.g. the ascending aorta. This because a morphometric analysis of the shape of the patient's blood vessel has been determined. This shape of the support can be such that the support surrounds the patient's blood vessel. In some embodiments, the support may be in substantially full contact with the blood vessel. The advantage of such a support is that the chances of the patient experiencing post-operative difficulties are reduced.

The support may have opposing longitudinal edges such that it may be formed into a tube by connecting the longitudinal edges together, e.g. by sewing (e.g. by placing locking stitches at intervals e.g. of about 10 mm), stapling, fusing, gluing or by an alternative method known to a person of skill in the art. The single piece support is optionally in the form of a sheet. The support may have a length which is similar (optionally substantially the same) as the length of the blood vessel. The support may have a width which is similar (optionally substantially the same) as the circumference of the blood vessel.

The tube formed by the support has a normal perimeter which provides a normal level of support and has a base level of hoop strength. Optionally, the normal effective perimeter of the tube formed by the support is substantially the same as the normal perimeter of the blood vessel. A blood vessel may have a plurality of regions wherein each of the regions has a different perimeter. In some embodiments, the support may have a plurality of normal regions wherein the normal (in other words, internal) perimeter of the tube formed by the support in each of the normal regions is substantially the same as the perimeter of the blood vessel in the respective region. One advantage of such features is that the support is shaped to be in morphological relationship with the blood vessel. Where it is said that the effective perimeter of the tube is "substantially the same" as the perimeter of the blood vessel in the respective region, it is meant that the effective perimeter of the tube is 10% more or less than the perimeter of the blood vessel, optionally 5% more or less, for example 1% more or less.

In some embodiments, the support according to the invention may be formed from a deformable material. A support is optionally formed from a plastically deformable material. The support may be in the form of a settable material. A settable material is a material which can be set in a particular shape by radiation (e.g. thermal, infrared or UV radiation) or chemical treatment, for example a heat-settable material.

In some embodiments, the settable material may be in the form of a mesh, especially a dense mesh. In some embodiments, the settable material may be in the form of a dense mesh where a thread used to form the mesh is a fine thread or where the mesh has a small aperture size. Optionally, the support may be formed from a knitted or a woven material; optionally it is formed from a knitted mesh. In some embodiments, the support may be formed from a physiologically acceptable material (e.g. a material suitable for use as a suture thread) e.g. a natural fibre (e.g. silk) and/or an artificial fibre (such as a medical grade polymer, e.g. nylon, polypropylene, polyester, polytetrafluoroethylene (PTFE) or polyethyleneteraphthalate). The support may be formed from a physiologically absorbable material. Optionally, the support may be sterilised.

The term mesh is used to mean a material having a plurality of apertures; optionally a mesh aperture is diamond shaped. In some embodiments, a mesh aperture may have a dimension selected to provide an appropriate range of support pressure on the blood vessel. One advantage of using a settable material in the form of a mesh is that the material automatically provides greater support when it is stretched because its hoop strength increases.

The blood vessel may have one or more regions which might benefit from a different degree of support or flexibility. For example, in a region where the blood vessel is weak, a greater degree of support may be optimal or at an end of a support, a lesser degree of support may be suitable. In some embodiments, the support may have one or more regions which has a characteristic designed to suit a corresponding region of a blood vessel. A suitable characteristic is that the region is more supportive, less supportive or more flexible than a normal region of the support. Optionally a region having such a characteristic is a circumferential region. In some embodiments, the support is pre-formed to have one or more such regions.

In some embodiments, the support has a first more supportive region having an increased hoop strength. One advantage of the first more supportive region is that the increased hoop strength relative to the base level of hoop strength enables the support to withstand a greater internal pressure thereby strengthening and/or providing more support to a weaker region of the blood vessel. In some embodiments, the first more supportive region has a similar bend or crush strength to a normal region so that the support behaves normally when subjected to bending and/or crushing forces e.g. in an emergency situation, for example during a road traffic accident. A further advantage of the first more supportive region is that such a region restricts movement of the support on the blood vessel and so such a region may be used to positively locate the support on the blood vessel. It is useful for the support to have a region which enables positive location of the support on the blood vessel. This is because when the support has a plurality of different regions each having a characteristic designed to provide suitable support to a corresponding region of a blood vessel, positively locating the support can ensure that each region is placed in proximity with its corresponding region on the blood vessel.

In some embodiments, the blood vessel may be a major blood vessel such as a portal vein, vena cava or the aorta; optionally, the blood vessel is a cardiac blood vessel or a blood vessel connected to the heart; optionally the blood vessel is the ascending aorta. In some embodiments, where the support is for use with the ascending aorta, a first more supportive region may be for use in supporting a trilobal section of the aorta, especially in the region of an aortic valve. One advantage of using a first more supportive region to support the trilobal section of the ascending aorta is that it helps keep the valve leaflets in place so that the valve operates without leakage.

In some embodiments, where the support is in the form of a mesh, a first more supportive region may be provided by a stretched area of the mesh. The support in such a region is deformed and has an increased hoop strength. A deformed region of the support may have a perimeter which is longer than the normal perimeter. In a deformed region of the mesh, an increase in hoop strength is obtained as mesh apertures formed by mesh threads narrow such that the threads used to form the mesh become almost parallel around the perimeter of the support.

In some embodiments, the support may have a second more supportive region wherein the thickness of the support is greater, optionally such a region has at least a double thickness of support. One advantage of the second more supportive region is that it provides increased support without restricting movement of the blood vessel. The second more supportive region may be useful to provide support in an area of a blood vessel proximal to a region requiring a greater degree of flexibility. A second more supportive region may also be useful to provide localised support, for example axial support. The support in a second more supportive region may also be deformed such that it has an increased hoop strength.

Where the blood vessel is an ascending aorta, a second more supportive region is suitable for use in supporting an aortic annulus which is the section of the ascending aorta proximal to the heart. In some embodiments, the second more supportive region may be provided at an end of the support; referred to herein as a proximal end of the support. In some embodiments, the second more supportive region may be shaped to be placed around an aortic annulus of the aorta which has a small depth. Optionally, the second more supportive region has a small enough depth to be inserted under the adjoining blood vessels or other tissues. In some embodiments, the small depth of the second more supportive region may be from about 2 mm (or from 4 mm) to 15 mm (or to 10 mm). A second more supportive region having a small depth is advantageous when the blood vessel is the ascending aorta because it eases the placement of this part of the support under the two coronary arteries that emerge from the aorta from the sinuses of valsalva close to the aortic annulus. Any large or rigid structure would be difficult to place in the confined space under these relatively fragile vessels.

One way in which a second more supportive region may be provided is by a hem at an end of the support. A hem is a region of the support wherein one end of the support has been folded over and connected to the support, e.g. by sewing, stapling, fusing, gluing or by an alternative method known to a person of skill in the art. If it is required that a hem should be more supportive, one or more further layers may be provided between the folded layers of the support.

In some embodiments, the second more supportive region may be provided axially such it is an axial second more supportive region. An advantage of an axial second more supportive region is that it affords additional localised axial support to the blood vessel. This can be useful because in some circumstances, when a weakened blood vessel dilates, it can also extend lengthwise. An axial second more supportive region may be an axial hem formed when the support is formed into a tube.

In some embodiments, the support may have a less supportive region having a decreased hoop strength. An advantage of a less supportive region is that it minimises the change between the support and native unsupported blood vessel where the blood vessel would otherwise be at a greater risk of rupture. Where the blood vessel is the ascending aorta and the less supportive region is provided at a distal end of the support, this part of the aorta is capable of significant movement and the risk of damage can be reduced by providing a less supportive region to enable a smooth transition between the support and the blood vessel.

In some embodiments, where the support is in the form of a mesh, a less supportive region may be provided by one or more gaps formed in the support. Where a less supportive region is provided at an end of the support, the less supportive region may be coronated. By "coronated" is meant that an end of the support is crown shaped, e.g. such that an end of the support is cut into a zigzag pattern. In a coronated region of the mesh or an area of the mesh otherwise having gaps formed in it, the support is in continuous contact with the blood vessel but has a lower hoop strength.

It has been found that if there is an area having an abrupt change in the size of the perimeter of the support between regions of the support having different perimeter lengths, the blood vessel is not adequately supported and is prone to rupture. Accordingly, it is preferred that in such an area, the size of the perimeter changes gradually to reduce the risk of rupture.

In some embodiments, the support may be provided on a former. Optionally the former has a similar shape to the blood vessel such that the former is supportive of the support to help maintain the shape of the support. An advantage of providing the support on such a shaped former is that it helps a surgeon in orientating the support for correct application to the blood vessel, particularly when the blood vessel has a complex shape.

In some embodiments, the support may be releasably mounted on the former. Optionally, the support is releasably mounted on the former by the opposing longitudinal edges of the support being releasably connected, for example by a releasable stitch (e.g. a single chain stitch), staple or glue. An advantage of using a single chain stitch is that this stitch can be undone in a single pull of the stitch or of a thread used to form the stitch. This means that the thread can be rapidly removed in order to open the support so that it can be placed around the aorta. It is useful if it is easy to release the support from the former. This is in order to minimise the time taken for the method of supporting a blood vessel according to the invention such that the length of time that the patient is under anaesthetic as well as the duration of the overall procedure is reduced, lowering the risks that are associated with this type of surgery.

In some embodiments, the method of supporting a blood vessel according to the invention may be performed without any interruption in the blood vessel (i.e. without cutting the blood vessel) or in the circulation. Where the support is provided on a former, the method of supporting a blood vessel according to the invention comprises a step of releasing the support from the former.

According to the present invention there is further provided a method of morphometric analysis of a patient's blood vessel using an imaging scanner which method comprises:

(i) obtaining a diametral cross-sectional image of the blood vessel;

(ii) obtaining a pseudo-transverse cross-section image of the blood vessel; and (iii) processing the images from steps (i) and (ii) to construct a morphometric model of the blood vessel.

An advantage of the method of morphometric analysis according to the invention is that fewer scanned images from an imaging scanner are required, reducing any difficulties experienced by the patient during the imaging. A morphometric model obtained by the method of morphometric analysis may be a three-dimensional model.

A scanner suitable for use in the method of morphometric analysis according to the invention may be a MRI, MRA, X-ray CT, or a 3D pulsed Doppler Echo imaging scanner; optionally the scanner is a MRI scanner.

Optionally step (i) of the method of morphometric analysis according to the invention comprises obtaining the image from a set of 2D images, e.g. a pseudo-transverse cross-sectional image and a set of diametral cross-sectional images. Where the blood vessel is a heart valve wall e.g. the ascending aorta, step (i) comprises obtaining a diametral cross-sectional image of the aortic annulus, left ventricular outflow tract, aortic valve and ascending aorta.

In some embodiments of the method of morphometric analysis according to the invention, processing step (iii) may comprise measuring one or more parameters from the images obtained in steps (i) and (ii) and using the one or more parameters to construct a three dimensional computer generated morphometric model of the blood vessel. A suitable parameter optionally includes a linear dimension, a circumferential dimension, and/or a rotational angle. The number of parameters required depends on the complexity of the blood vessel. For a complex blood vessel such as the ascending aorta, from 20 to 40 parameters may be needed. Step (iii) of the method of morphometric analysis optionally uses a computer running computer aided design (CAD) software to construct an model of the blood vessel.

The morphometric model of a blood vessel in the form of a heart valve wall or ascending aorta can be constructed using a relatively small number of parameters from the images obtained from steps (i) and (ii) of the method of morphometric analysis. The advantages of such a morphometric model include that anomalies caused by patient movement are accounted for, which produces a smooth model. The data set is vastly reduced and the modelling can be performed by medical staff who do not need to have CAD skills. The primary disadvantage is that the parameterization reduces the flexibility of the modelling procedure and may not be suitable for heavily distended aortas.

The morphometric model has a pseudo-sagittal plane which splits the ascending aorta into two halves. Near the root of the ascending aorta, these two planes are substantially mirror images of each other. At the aortic root plane, the cross section is circular, the model is perpendicular. Below this plane, the model is partially trilobal, above this plane the model curves. At the trilobal plane, the cross-sectional area is trilobal and has a maximumal cross section. The model is perpendicular to the trilobal plane as well. The aortic annulus plane determines the bottom of the trilobal section and the cross section of this plane is substantially circular. Below this plane the model has a substantially constant diameter.

Twenty seven parameters determine the shape of the stent and the position of the coronary arteries.

To determine the shape of the cross section at the trilobal plane of the model, nine parameters are measured. They are the radius of each lobe, the width of each lobe and the angle of each lobe relative to the pseudo-sagittal plane.

To determine the shape of the trilobal solid, four parameters are measured which are the diameters at the aortic annulus plane and aortic root plane and the distances from the aortic annulus plane and from the aortic root plane to the trilobal plane. Along with the parameters which determine the shape of the trilobal cross-section, these parameters determine the shape of the valve reconstruction.

To determine the shape of the curvature of the aorta above the valve, six parameters are required. The shape of the curvature is less than about 25% of the perimeter of an ellipse, followed by a tangential extension. The parameters are the aorta ellipse horizontal axis, the aorta ellipse vertical axis, the aorta radius at the end of the ellipse and the ratio of the horizontal projection to the horizontal axis, the distance of extension from end of ellipse and the diameter of the end of the extension.

The coronary arteries are each marked on the model by a small horizontal hole of arbitrary size. The position of each is determined by the distance from the base and the angle from the aortic plane. Two parameters are also used to characterise the coronary arteries which are the diameter of each artery.

The wall thickness of the solid former and base extension are two further critical parameters. They are of no significance to the shape of the support, but affect the cost, stiffness, strength and stability of a former used in the manufacturing process.

The model of the blood vessel (e.g. in the form of a CAD model) can then be used to manufacture a former from which the support of the invention can be made. A former is a physical model of a blood vessel. Depending on the manufacturing method employed, the former can be made as follows: the CAD model file can be transferred to an appropriate Rapid Prototyping machine, e.g. a stereo lithography machine (SLA) to produce a physical model (or a former) of the blood vessel in a polymer, e.g. UV curable epoxy resin. This model can then be used to produce a mould in silicone rubber. The mould can then be used to produce daughter models of the blood vessel, e.g. to be used as a former in the invention. Other manufacturing techniques can be used, for example selective laser sintering (SLS), CNC machining etc. Of these methods, SLS can be advantageous because the polymer(s) generally used are able to withstand being heated during a sterilisation process (where they might be heated to 134° C. for 26 minutes) or during a heat setting process.

The former produced by the above method may then be used in one of a number of manufacturing processes to make the finished support. In one method of manufacturing the finished support, a blank settable support is drawn over the former so that it is deformed to adopt a shape that morphometrically corresponds to the shape of the former. The support is then subjected to a setting treatment such that it retains the morphometric shape of the former, for example it may be heat set.

According to the invention there is also provided a method of manufacturing of manufacturing a support according to the invention which method comprises the steps of the method of morphometric analysis according to the invention and:

(iv) constructing a former from the morphometric model of the blood vessel obtained from the method of morphometric analysis;

(v) applying a blank support to the former; and (vi) setting the blank support to form a support according to the invention which has a morphological relationship with the blood vessel.

In some embodiments, step (iv) of the method of manufacturing according to the invention comprises stretching the blank support over regions of the former where a first more supportive area is required. In some embodiments, step (v) of the method of manufacturing according to the invention comprises setting the stretched areas of the blank support and shrink fitting other areas of the blank support.

According to the invention there is further provided a method of supporting a blood vessel which method comprises the steps of:

(i) applying to the blood vessel of a human or animal patient in need of such treatment a support according to the invention having longitudinal edges; and (ii) connecting the longitudinal edges such that the support forms a tube surrounding the blood vessel.

Where a support according to the invention has one or more regions which has a characteristic designed to suit a corresponding region of a blood vessel, step (i) of the method of supporting a blood vessel according to the invention comprises applying to the blood vessel of a human or animal patient in need of such treatment a support according to the invention having longitudinal edges such that the one or more regions having a characteristic designed to suit a corresponding region of a blood vessel are located proximal to the corresponding region(s) of the blood vessel.

An animal patient to be treated by the method of support according to the invention may be a mammal, for example a farm animal or domesticated animal.

Figure 7:
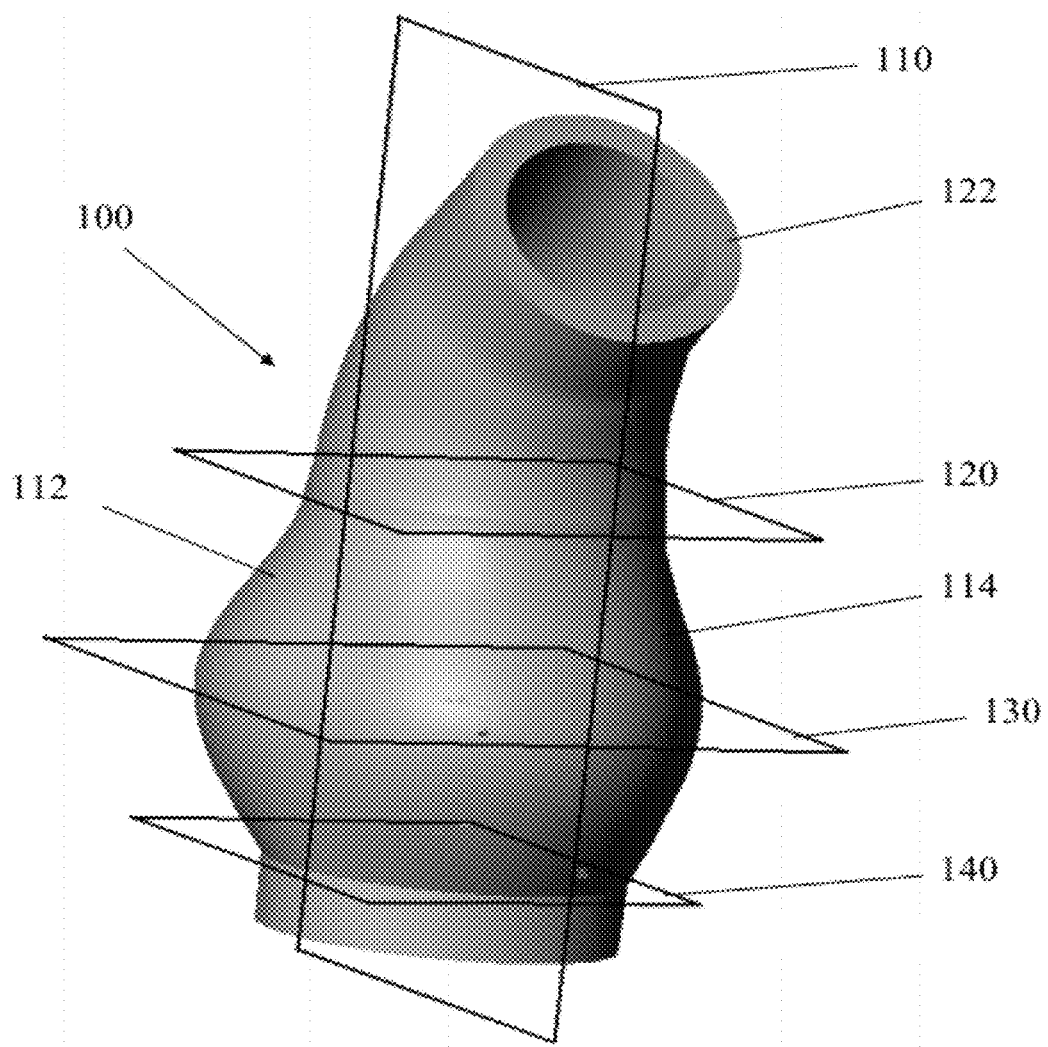
FIG. 7 shows a morphometric model of an ascending aorta and aortic arch.

FIG. 7 depicts a morphometric model of an ascending aorta and aortic arch indicated generally at 100. In FIG. 7, for ease of reference, specific construction planes are labelled. The pseudo-sagittal plane 110 splits the ascending aorta into two halves 112,114. Near the root, these two halves 112,114 are substantially mirror images of each other. At the aortic root plane 120, the cross section of the model 100 is circular, and the model 100 ascends perpendicularly from this plane. Below this plane 120, the model 100 is partially trilobal, above this plane the model 100 is curved because it is the start of the aortic arch 122.

At the trilobal plane 130, the cross section of the model 100 is trilobal and of maximum cross section. The model 100 is perpendicular to plane 130 as well.

The aortic annulus plane 140 is at the bottom of the trilobal part of the ascending aorta. The cross section of the model 100 at the aortic annulus plane 140 is circular. Below plane 140, the cross section of model 100 is of constant diameter.

FIGS. 8 to 10 show a support according to the invention indicated generally at 200. Support 200 can be seen to have the shape of the ascending aorta such that it has a morphological relationship with that blood vessel. This is because shape (or morphology) of the support 200 substantially corresponds (or relates) to the shape (or morphology) of the ascending aorta.

Support 200 is shown in FIG. 9 to be formed from knitted fine threads 202 which form diamond-shaped mesh apertures 204 such that the support 200 is in the form of a closed cell, dense mesh material having a substantially uniform thickness. The support 200 has longitudinal edges 232 and 234 which are joined at longitudinal seam 230 by seam thread 236 such that support 200 is in the form of a tube.

The support 200 has a length defined by longitudinal seam 230. The length of the support 200 is substantially the same as the length of the blood vessel to be supported. The support 200 has a width which is substantially the same as the circumference of the blood vessel to be supported. The support 200 has a proximal end indicated at 205 which, in use, is located at or near the aortic annulus plane. The support 200 also has a distal end indicated at 210 which, in use, is located at or near the aortic arch.

The support 200 has a first more supportive region indicated generally at 220. In use, this is located between the aortic root plane and the aortic annulus plane, particularly around the trilobal plane which has the maximum cross-section. In the first more supportive region 220, the mesh material is stretched, as shown in FIG. 10, such that its width is greater than the width of the support 200 at the proximal end 205. In the expanded view shown in FIG. 10 of the first more supportive region 220, the diamond-shaped mesh apertures 226 formed by the support 200 are elongated such that a circumferential dimension 224 of each mesh aperture 226 is longer than its longitudinal dimension 228. In comparison, a circumferential dimension (not shown) of mesh aperture 204 in a normal region of the support 200 is substantially the same as its longitudinal dimension (not shown).

The support 200 has a second more supportive region in the form of a hem 240. In use, this is located below the aortic annulus plane. Hem 240 has a double thickness of the support 200. A less supportive region 212 is provided at the distal end of the support 200 which, in use, is located at the aortic arch. The less supportive region 212 is coronated (not shown).

The invention is illustrated by the following Example which is not intended to limit the scope of the claims.

EXAMPLE 1

In the following Example, an illustration of the imaging method of the invention is given.

A patient is presented at an MRI unit for a conventional clinical MRI session to provide the clinician/surgeon with morphological and dimensional information from the patient's cardiac structures. As part of this process additional specific images are collected to form the basis of the manufacturing process for the support. A transaxial imaging plane is set up through the patient (front to back, horizontally through a (standing) patient) to give a horizontal cross section through the patient. This plane is then adjusted to a pseudo-transaxial position perpendicular to the patient's ascending aorta (at the aortic valve level). A set of image slices is then obtained from the aortic annulus (Left Ventricular Outflow Tract [LVOT]), up through the aortic valve and up the ascending aorta to the aortic arch.

These image data are processed using a dedicated computer aided design (CAD) routine which takes specific measurements of various of the aortic structures including the twenty seven parameters identified above which determine the shape of the stent and the position of the coronary arteries. The parameters are the radius of each lobe, the width of each lobe and the angle of each lobe relative to the pseudo-sagittal plane, the diameters at the aortic annulus plane and aortic root plane and the distances from the aortic annulus plane and from the aortic root plane to the trilobal plane, the aorta ellipse horizontal axis, the aorta ellipse vertical axis, the aorta radius at the end of the ellipse and the ratio of the horizontal projection to the horizontal axis, the distance from the base of each coronary artery and their angle from the aortic plane, the distance of extension from end of ellipse, the diameter of the end of the extension, the diameter of each coronary artery, the wall thickness of the solid former and base extension.

These quantitative data are processed by the CAD routine to produce a 3D reconstruction of the patient's aorta from the aortic annulus (LVOT) to the aortic arch at the Brachiocephalic branch. The CAD model is then converted to a suitable file format and exported to an appropriate Rapid Prototyping (RP) machine. The RP machine then produces a rigid 1:1 scale model of the patient's aorta in a suitable thermoplastic. The model includes surface morphology and positional markings of coronary origins.

EXAMPLE 2

In this Example, an illustration of the preparation of a support according to the invention is given.

The thermoplastic model of the patient's aorta prepared according to Example 1 provides a former upon which the external support may be manufactured. This is done by manufacturing a blank tubular support, whose inside diameter relates to the patient's aortic annular diameter, from a medical grade textile mesh. The mesh is manufactured from a medical grade polymer, for example, PolyTetraFluoroEthylene (PTFE) or PolyEthyleneTeraphalate (PET).

The blank support is cylindrical and includes a narrow circumferential hem at the proximal end (which in use would be applied to the LVOT), and an axial hem that can be opened by the surgeon prior to placing the support around the patient's aorta.

The blank support is drawn onto the thermoplastic former and positioned such that when the support is applied to the patient's aorta during surgery, the axial hem will be accessible to the surgeon. The blank support is then heat set around the former so as to incorporate all of the former's surface morphology into the mesh support. This can be effected by any convenient means e.g. in a laboratory oven. The finished support, still on its manufacturing former, is then sterilised, packaged and sent to the surgeon.

In an alternative embodiment, if minor aortic valve regurgitation is present, a former may be scaled to an undersize, e.g. 90% or 85% of the patient's actual size, so as to impose a minor reduction in aortic dimension so as to correct this malfunction.

EXAMPLE 3

In this Example, an illustration is given of the use of the support prepared in Example 2 to support the patient's blood vessel.

With the patient anaesthetised, the thorax opened and the ascending aorta dissected clear of its adjacent structures, the surgeon is able, with the help of the in-situ former, to orientate the support prepared as described in Example 2 with respect to the 3 valve lobes (sinuses) prior to implanting it. The axial seam is then opened and the support removed from its manufacturing former. Clearance accommodations for the coronary origins (marked on the former) are cut into the support from each side of the axial hem. The proximal end of the support is then sutured into the ventricular tissues adjacent the aortic annulus. The axial hem is then closed up the length of the support and an accommodation cut around the base of the brachiocephalic artery on the aortic arch. This completes the location of the support. Trans oesophagel echocardiography is then used to confirm aortic valve competence and normal coronary blood flow. The patient's thorax can then be closed.

In an alternative embodiment, if minor aortic valve regurgitation is present, on implantation, the patient's blood pressure is reduced in a controlled fashion until the aorta shrinks uniformly to a size at which a reduced size support will fit. The support is then implanted, blood pressure is returned to normal and valve function and coronary blood flow checked as above. In this way mild regurgitation can be recovered.

The invention claimed is:

1. A support adapted for location exteriorly of an ascending aorta, wherein the ascending aorta has an aortic valve, the support comprising:
    a tubular support body comprising a mesh, a proximal portion having a proximal portion hoop strength, a distal portion having a distal portion hoop strength, and opposing longitudinal edges which are joined together by a zip fastener, thread, staple or glue;
    the proximal portion further comprising a most proximal region adapted for use in supporting the region of the aortic valve, wherein the most proximal region is a hem;
    wherein the proximal portion hoop strength is greater than the distal portion hoop strength; and
    the tubular support body is pre-formed with a shape that morphometrically corresponds to the shape of the ascending aorta.

2. A support as defined in claim 1 wherein the mesh is formed from a settable material.

3. A support as defined in claim 1 wherein thickness of the hem is greater than thickness of the distal portion.

4. A support as defined in claim 1 wherein thickness of the hem is at least double of thickness of the distal portion.

5. A support as defined in claim 2 wherein the mesh having a plurality of apertures.

6. A support as defined in claim 5 wherein one or more of the plurality of apertures is diamond shaped.

7. A method of treating aortic root dissection in a patient having an ascending aorta in need of such treatment, wherein the ascending aorta has an outer surface and an aortic valve, using the support of claim 1, the method comprises the steps of:
    (i) applying the tubular support body to the outer surface of the ascending aorta;
    (ii) connecting the longitudinal edges to secure the tubular support body to the outer surface of the ascending aorta such that the tubular support body forms a tube surrounding the ascending aorta.

8. A method of treating aortic root dissection in a patient having an ascending aorta in need of such treatment, wherein the ascending aorta has an outer surface and an aortic valve, using the support of claim 1, the method comprises the steps of:
  (i) applying the support to the outer surface of the ascending aorta, wherein prior to the step of applying, the support is provided on a former and wherein the method further comprises an initial step of releasing the support from the former.

9. A support as defined in claim 1 wherein the mesh is formed from a knitted material.

* * * * *